(12) United States Patent
Kensicher et al.

(10) Patent No.: US 11,753,496 B2
(45) Date of Patent: Sep. 12, 2023

(54) SOFTENING COMPOSITION

(71) Applicant: COATEX, Genay (FR)

(72) Inventors: Yves Kensicher, Theize (FR); Benoit Magny, Cailloux sur Fontaine (FR); Yves Matter, Quincieux (FR); Jean-Marc Suau, Lucenay (FR)

(73) Assignee: COATEX, Genay (FR)

( * ) Notice: Subject to any disclaimer, the term of this patent is extended or adjusted under 35 U.S.C. 154(b) by 528 days.

(21) Appl. No.: 16/762,978

(22) PCT Filed: Dec. 14, 2018

(86) PCT No.: PCT/FR2018/053292
§ 371 (c)(1),
(2) Date: May 11, 2020

(87) PCT Pub. No.: WO2019/122629
PCT Pub. Date: Jun. 27, 2019

(65) Prior Publication Data
US 2020/0277431 A1    Sep. 3, 2020

(30) Foreign Application Priority Data
Dec. 19, 2017    (FR) ...................... 1762529

(51) Int. Cl.
| | |
|---|---|
| *C08G 18/00* | (2006.01) |
| *C08G 18/28* | (2006.01) |
| *A61K 8/87* | (2006.01) |
| *A61Q 5/12* | (2006.01) |
| *C08G 18/22* | (2006.01) |
| *C08G 18/48* | (2006.01) |
| *C08G 18/71* | (2006.01) |
| *C08G 18/75* | (2006.01) |
| *C08G 18/76* | (2006.01) |
| *C08K 5/19* | (2006.01) |
| *C11D 3/00* | (2006.01) |
| *C11D 11/00* | (2006.01) |

(52) U.S. Cl.
CPC ............ *C08G 18/2825* (2013.01); *A61K 8/87* (2013.01); *A61Q 5/12* (2013.01); *C08G 18/227* (2013.01); *C08G 18/4833* (2013.01); *C08G 18/71* (2013.01); *C08G 18/755* (2013.01); *C08G 18/7621* (2013.01); *C08K 5/19* (2013.01); *C11D 3/0015* (2013.01); *C11D 11/0017* (2013.01); *A61K 2800/48* (2013.01)

(58) Field of Classification Search
CPC .............. C08G 18/2825; C08G 18/227; C08G 18/4833; C08G 18/71; C08G 18/755; C08G 18/7621; C08G 18/282; C08G 18/711; C08G 18/792; A61K 8/87; A61K 2800/48; A61Q 5/12; C08K 5/19; C11D 3/0015; C11D 11/0017; C11D 1/62; C11D 3/3726; C11D 7/5013; D06M 2200/40; D06M 2200/50; D06M 15/568; D06M 13/46; C08L 75/04
USPC ........................................................ 524/591
See application file for complete search history.

(56) References Cited

U.S. PATENT DOCUMENTS

| | | | | |
|---|---|---|---|---|
| 3,923,713 A | * | 12/1975 | Hermann | ............... C09J 175/08 |
| | | | | 528/905 |
| 4,180,491 A | * | 12/1979 | Kim | ...................... C08G 18/71 |
| | | | | 524/391 |
| 2010/0152375 A1 | * | 6/2010 | Kensicher | ................. A61K 8/86 |
| | | | | 524/591 |
| 2013/0053299 A1 | | 2/2013 | Koehle et al. | |

FOREIGN PATENT DOCUMENTS

| | | | |
|---|---|---|---|
| FR | 2 372 865 A1 | 6/1978 | |
| FR | 2 894 980 A1 | 6/2007 | |
| GB | 1601220 A * | 10/1981 | .............. C08L 75/08 |
| WO | WO 2018/073545 A1 | 4/2018 | |
| WO | WO 2018073545 * | 4/2018 | ............... C09D 7/00 |

OTHER PUBLICATIONS

International Search Report dated May 3, 2019 in PCT/FR2018/053292 filed on Dec. 14, 2018, 2 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

The invention relates to the field involving the softening or lubricating of natural, synthetic or mixed textile fibres, as well as keratin fibres. The invention provides a softening composition, the rheology of which is controlled by means of a particular thickening agent. The invention also relates to the thickening agent, which is made from multiple isocyanate compounds.

17 Claims, No Drawings

SOFTENING COMPOSITION

The invention relates to the field of softening or lubrication of textile, natural, synthetic or mixed fibres and keratin fibres. The invention provides a conditioning or softening composition the rheology of which is controlled by a special thickening agent. This thickening agent, prepared from several isocyanate compounds, is also part of the invention.

Fibre conditioning, in particular softening or lubrication, usually helps to prevent various phenomena that cause deterioration of the properties of these fibres or even deterioration of the fibres themselves. Such deterioration may occur in textile fibres but also in keratin fibres, in particular in hair.

To effectively develop their properties, such as improving the appearance and feel of the fibres, lubricating the fibres and reducing wear due to friction, limiting static load build-up, or accelerating drying, the softening compositions must be homogeneous, in particular by avoiding any granular or greasy formation. They must have a controlled viscosity so that they can be easily and effectively used, particularly when poured. Their viscosity must also be compatible with the settings of automatic devices in which they may be used, in particular laundry washing machines.

They should also be stable over time and should not turn yellow.

These softening compositions must also have good antistatic properties.

Moreover, it is important to have softening compositions that are easy to handle, especially when dosing. Indeed, when using these softening compositions, it is essential that the amount used can be accurately controlled.

Softening compositions should also be sufficiently concentrated in active substances, in particular to limit the volumes implemented or improve their manufacturing and transporting conditions.

Document WO 2018/073545 A1 relates to a urethane compound that changes the rheology of coating compositions comprising mineral particles, particularly paint compositions. Document FR 2 372 865 describes thickening compositions comprising a non-ionic polyurethane, a surfactant, a non-aqueous inert diluent, and water to thicken textile print stock. Document FR 2 894 980 A1 discloses clear aqueous thickening compositions containing non-ionic surfactants and a polyurethane compound for thickening clear acidic formulations. Document EP 2 563 889 A1 describes a softening composition for fabrics comprising a tertiary or quaternary ammonium salt and a non-ionic softening compound.

There are known thickening agents that do not provide an effective solution to the problems encountered, in particular problems relating to the viscosity and stability of the softening compositions in which they are present.

It is therefore necessary to have thickening agents that make it possible to prepare effective softening compositions with improved viscosity and stability. These thickening agents must also have good compatibility with the various components of the softening compositions.

The invention makes it possible to provide a solution to all or part of the problems encountered with the thickening agents in compositions in the prior art.

Thus, the invention provides a thickening agent comprising:
I. at least one compound, prepared in the absence of any diisocyanate compound, by reaction:
  (A) of at least one monoisocyanate compound chosen among:
    (A1) a compound comprising a single isocyanate group and
    (A2) at least one monoisocyanate compound from the separate reaction
      (A2-1) of at least one compound comprising at least one labile hydrogen atom and
      (A2-2) of at least one asymmetric diisocyanate compound,
  (B) of at least one isocyanate compound comprising more than 2 isocyanate groups, and
  (C) of at least one compound of formula (I):

$$(\text{HO})\text{-L}_n\text{-(OH)} \qquad (I)$$

wherein L independently represents a polyalkylene glycol residue and n represents a number ranging from 40 to 400; and
II. at least one non-aromatic solvent, non-reactive with the isocyanate group and chosen among ketones, ethers, aprotic ethyl derivatives, diethers, crown ethers, esters, diesters, carbonates, furans, halogenated solvents, alkanes, alkenes, alcynes, solvents from renewable resources, nitrogenous or sulphurous solvents, mineral oils, silicone oils, and combinations thereof.

The thickening agent according to the invention therefore comprises at least one compound (I) prepared in the absence of any diisocyanate compound, and at least one solvent (II) that is non-aromatic and non-reactive with the isocyanate group.

Preferably, the thickening agent according to the invention is prepared from a monoisocyanate compound (A1) of formula (II):

$$\text{R—NCO} \qquad (II)$$

wherein R represents a straight, branched or cyclic saturated, unsaturated or aromatic hydrocarbon group, preferably a straight, branched or cyclic saturated, unsaturated, or aromatic hydrocarbon group comprising from 8 to 40 carbon atoms or a straight, branched or cyclic alkyl group comprising from 8 to 40 carbon atoms or a straight, branched, or cyclic alkenyl group comprising from 8 to 40 carbon atoms.

More preferably, the thickening agent according to the invention is prepared from a monoisocyanate compound (A1) of formula (II) wherein R represents a straight, branched or cyclic saturated, unsaturated or aromatic hydrocarbon group comprising from 10 to 32 carbon atoms or from 10 to 30 carbon atoms, preferably from 12 to 24 carbon atoms, more preferentially from 14 to 22 carbon atoms.

Also more preferably, the thickening agent according to the invention is prepared from a monoisocyanate compound (A1) of formula (II) wherein R represents a straight, branched or cyclic alkyl group comprising from 10 to 32 carbon atoms or from 10 to 30 carbon atoms, preferably from 12 to 24 carbon atoms, more preferentially from 14 to 22 carbon atoms.

Also more preferably, the thickening agent according to the invention is prepared from a monoisocyanate compound (A1) of formula (II) wherein R represents a straight, branched, or cyclic or aromatic alkenyl group comprising from 10 to 32 carbon atoms or from 10 to 30 carbon atoms, preferably from 12 to 24 carbon atoms, more preferentially from 14 to 22 carbon atoms.

Particularly preferably, the thickening agent according to the invention is prepared from a monoisocyanate compound (A1) of formula (II) wherein R represents a straight, branched, or cyclic saturated, unsaturated or aromatic hydrocarbon group comprising from 14 to 22 carbon atoms, particularly a straight, branched or cyclic alkyl group comprising from 14 to 22 carbon atoms or a straight, branched, or cyclic or aromatic alkenyl group comprising from 14 to 22 carbon atoms.

Also particularly preferably, the thickening agent according to the invention is prepared from a monoisocyanate compound (A1) of formula (II) wherein R represents:
- a straight, branched or cyclic alkyl group comprising from 8 to 19 carbon atoms or from 8 to 18 carbon atoms; or
- a straight, branched, or cyclic or aromatic alkenyl group comprising from 8 to 19 carbon atoms or from 8 to 18 carbon atoms.

Also particularly preferably, the thickening agent according to the invention is prepared from a monoisocyanate compound (A1) of formula (II) wherein R represents:
- a straight, branched, or cyclic alkyl group comprising from 8 to 11 carbon atoms or 13 carbon atoms or from 15 to 18 carbon atoms or from 15 to 19 carbon atoms; or
- a straight, branched, or cyclic or aromatic alkenyl group comprising from 8 to 11 carbon atoms or from 8 to 11 carbon atoms or 13 carbon atoms or from 15 to 18 carbon atoms or from 15 to 19 carbon atoms.

Also particularly preferably, the thickening agent according to the invention is prepared from a monoisocyanate compound (A1) of formula (II) wherein R represents:
- a straight, branched, or cyclic alkyl group comprising from 21 to 40 carbon atoms or from 21 to 32 carbon atoms or from 22 to 40 carbon atoms or from 22 to 32 carbon atoms; or
- a straight, branched, or cyclic or aromatic alkenyl group comprising from 21 to 40 carbon atoms or from 21 to 32 carbon atoms or from 22 to 40 carbon atoms or from 22 to 32 carbon atoms.

Also particularly preferably, the thickening agent according to the invention is prepared from a monoisocyanate compound (A1) chosen among:
- the aromatic monoisocyanate compounds, in particular phenyl isocyanate, diphenyl methane monoisocyanate, 2-phenylethyl isocyanate, 4-tolyl isocyanate, 2-tolyl isocyanate, 2,5-dimethylphenyl isocyanate, 3,4-dimethylphenyl isocyanate, 2,3-dimethylphenyl isocyanate, 4-isocyanato-4'-methyldiphenylmethane;
- the polyfunctional aromatic monoisocyanate compounds, in particular 2-methoxy-4-nitrophenyl isocyanate, polymethylene polyphenyl isocyanate;
- the alkyl monoisocyanate compounds, in particular hexyl isocyanate, heptyl isocyanate, octyl isocyanate, n-nonyl isocyanate, decyl isocyanate, undecyl isocyanate, dodecyl isocyanate, tridecyl isocyanate, tetradecyl isocyanate, cetyl isocyanate, 2-ethylhexyl isocyanate, n-octyl isocyanate, isononyl isocyanate, stearyl isocyanate, decyl isocyanate, undecyl isocyanate, dodecyl isocyanate, tridecyl isocyanate, tetradecyl isocyanate, cetyl isocyanate, behenyl isocyanate, lignoceryl isocyanate, cerotyl isocyanate, eicosanyl isocyanate;
- the cycloalkyl monoisocyanate compounds, in particular cyclohexyl isocyanate, 1-isocyanatomethyl-1,3,3-trimethylcyclohexane;
- the unsaturated monoisocyanate compounds, in particular myristolyl isocyanate, palmitoleyl isocyanate, sapienyl isocyanate, oleyl isocyanate, elaidyl isocyanate.

As a monoisocyanate compound (A1) implemented according to the especially preferred invention, we can list:
- the saturated monoisocyanate compounds, in particular decyl isocyanate, undecyl isocyanate, dodecyl isocyanate, tridecyl isocyanate, tetradecyl isocyanate, cetyl isocyanate, stearyl isocyanate, behenyl isocyanate, lignoceryl isocyanate, cerotyl isocyanate, eicosanyl isocyanate;
- the unsaturated monoisocyanate compounds, in particular myristolyl isocyanate, palmitoleyl isocyanate, sapienyl isocyanate, oleyl isocyanate, elaidyl isocyanate, linoleyl isocyanate, linolenyl isocyanate, arachidonyl isocyanate, eicosapentanyl isocyanate.

According to the invention, the compound (I) can be prepared from a monoisocyanate compound (A) which is a compound (A1) or a compound (A2). Compounds (A1) and (A2) are not diisocyanate compounds.

Compound (A2) can nevertheless be prepared from a compound (A2-1) which comprises at least one labile hydrogen atom and at least one diisocyanate compound which is an asymmetric diisocyanate compound.

Preferably according to the invention, the compound (A2-1) is chosen from a compound comprising at least one labile hydrogen atom that is reactive with the asymmetric diisocyanate compound.

Preferably according to the invention, the compound (A2-1) is a compound comprising at least one hydroxyl group; a compound comprising a primary amine group or a secondary amine group; a carboxylic acid; a mercaptan compound.

More preferably according to the invention, the compound (A2-1) is a compound comprising a hydroxyl group. This is in particular a monohydric alcohol, e.g., a straight, branched or cyclic $C_8$-$C_{40}$ or $C_8$-$C_{32}$ monohydric alcohol, preferably $C_{10}$-$C_{30}$, more preferentially $C_{12}$-$C_{24}$, even more preferentially $C_{14}$-$C_{22}$.

Preferably according to the invention, the compound (A2-2) is chosen among the asymmetric aromatic diisocyanate compounds and the asymmetric alicyclic diisocyanate compounds.

More preferably according to the invention, the compound (A2-2) is chosen among 2,4'-diphenylmethylene diisocyanate (2,4'-MDI), 2,4'-dibenzyl diisocyanate (2,4'-DBDI), 2,4-toluene diisocyanate (2,4-TDI); isophorone diisocyanate (IPDI).

Moreover, and fundamentally according to the invention, the asymmetric character of the diisocyanate compound (A2-2) leads to a different reactivity of the two isocyanate groups it comprises. Indeed, both isocyanate groups generally have different reaction kinetics. Thus, the urethane compound according to the invention is functionalised in a controlled manner.

According to the invention, the compound (I) is prepared from a compound (A) and a compound (B) comprising more than two isocyanate groups. Compound (B) is thus not a diisocyanate compound.

Preferably according to the invention, compound (B) is an isocyanate compound comprising more than 2.2 isocyanate groups or more than 2.5 isocyanate groups, preferably more than 2.6 isocyanate groups, more preferentially more than 2.7 isocyanate groups or more than 3 isocyanate groups.

Also preferably according to the invention, compound (B) is an isocyanate compound comprising from 2.2 to 6 isocyanate groups, from 2.2 to 5 isocyanate groups, from 2.2 to 4 isocyanate groups, from 2.2 to 3.5 isocyanate groups, from 2.5 to 6 isocyanate groups, from 2.5 to 4 isocyanate groups, from 2.5 to 3.5 isocyanate groups, in particular from 2.6 to 3.3 isocyanate groups.

More preferably according to the invention, compound (B) is an isocyanate compound comprising from 2.2 to 3.5 isocyanate groups, from 2.5 to 6 isocyanate groups, from 2.5 to 4 isocyanate groups, from 2.5 to 3.5 isocyanate groups, in particular from 2.6 to 3.3 isocyanate groups.

Also more preferably according to the invention, compound (B) is a compound chosen among:
triphenylmethane-4,4',4"-triisocyanate or 1,1',1"-methylidynetris (4-isocyanatobenzene);
an isocyanurate compound, in particular an isocyanurate compound of a compound chosen among:
the symmetrical aromatic diisocyanate compounds, preferably:
2,2'-diphenylmethylene diisocyanate (2,2'-MDI) and 4,4'-diphenylmethylene diisocyanate (4,4'-MDI);
4,4'-dibenzyl diisocyanate (4,4'-DBDI);
2,6-toluene diisocyanate (2,6-TDI);
m-xylylene diisocyanate (m-XDI);
the symmetrical alicyclic diisocyanate compounds, preferably methylene bis(4-cyclohexylisocyanate) ($H_{12}$MDI);
the symmetrical aliphatic diisocyanate compounds, preferably hexamethylene diisocyanate (HDI), pentamethylene diisocyanate (PDI);
the asymmetric aromatic diisocyanate compounds, preferably:
2,4'-diphenylmethylene diisocyanate (2,4'-MDI);
2,4'-dibenzyl diisocyanate (2,4'-DBDI);
2,4-toluene diisocyanate (2,4-TDI);
a biuret trimer compound, in particular a biuret trimer compound of a compound chosen among:
the symmetrical aromatic diisocyanate compounds, preferably:
2,2'-diphenylmethylene diisocyanate (2,2'-MDI) and 4,4'-diphenylmethylene diisocyanate (4,4'-MDI);
4,4'-dibenzyl diisocyanate (4,4'-DBDI);
2,6-toluene diisocyanate (2,6-TDI);
m-xylylene diisocyanate (m-XDI);
the symmetrical alicyclic diisocyanate compounds, preferably methylene bis(4-cyclohexylisocyanate) ($H_{12}$MDI);
the symmetrical aliphatic diisocyanate compounds, preferably hexamethylene diisocyanate (HDI), pentamethylene diisocyanate (PDI);
the asymmetric aromatic diisocyanate compounds, preferably:
2,4'-diphenylmethylene diisocyanate (2,4'-MDI);
2,4'-dibenzyl diisocyanate (2,4'-DBDI);
2,4-toluene diisocyanate (2,4-TDI);
the asymmetric alicyclic diisocyanate compounds, preferably isophorone diisocyanate (IPDI).

Particularly preferably according to the invention, compound (B) is a compound chosen among triphenylmethane-4,4',4"-triisocyanate, 1,1',1"-methylidynetris (4-isocyanatobenzene), an HDI isocyanurate, an IPDI isocyanurate, a PDI isocyanurate, an HDI biuret trimer, an IPDI biuret trimer and a PDI biuret trimer.

In addition to compounds (A) and (B), the compound (I) according to the invention is prepared from a compound (C). Compound (C) is a compound of formula (I).

Preferably, compound (C) is a compound of formula (I) wherein:
L independently represents a polyethylene glycol residue; or
n represents a number ranging from 50 to 400, preferably from 100 to 300; or
L independently represents a polyethylene glycol residue and n represents a number ranging from 50 to 400, preferably from 100 to 300.

According to the invention, the molecular mass of the compound (C) implemented may vary. According to the invention, the molecular mass is calculated from the hydroxyl index determined in accordance with standard DIN 53240-1, now standard DIN EN ISO 4629-1, by applying the formula: (56,100×functionality in OH groups)/hydroxyl index. Preferably, the compound (C) of formula (I) has a molecular mass ($M_w$) ranging from 1,500 to 20,000 g/mol. Preferably, this molecular mass ($M_w$) ranges from 2,000 to 20,000 g/mol, more preferentially 4,000 to 15,000 g/mol.

When preparing the compound (I) implemented according to the invention, the respective amounts of compounds (A), (B) and (C) may vary. In particular, the molar amount of monoisocyanate compound (A) may be higher than the molar amount of compound (C). Preferably, the molar amount of monoisocyanate compound (A) is approximately twice as high as the molar amount of compound (C).

In addition to the compound (I), the thickening agent according to the invention comprises at least one solvent (II). According to the invention, the solvent (II) is non-reactive with isocyanate group.

The thickening agent according to the invention advantageously comprises a single solvent (II). However, it may comprise two, three or four different solvents (II).

Preferably according to the invention, solvent (II) is non-aromatic, aprotic, and non-reactive with the isocyanate group.

The non-aromatic solvent (II) is chosen among ketones, ethers, aprotic ethyl derivatives, diethers, crown ethers, esters, diesters, carbonates, furans, halogenated solvents, alkanes, alkenes, alcynes, solvents from renewable resources, nitrogenous or sulphurous solvents, mineral oils, silicones oils and combinations thereof.

Advantageously according to the invention, the non-aromatic solvent (II) is chosen among:
acetone, acetophenone, butanone, cyclopentanone, ethylpropyl ketone, 2-hexanone, isophorone, methylbutyl ketone, methyl 2-pentanone,
the polyalkylene glycol dialkyl ethers, e.g. ethylene glycol dimethyl ether, ethylene glycol diethyl ether, ethylene glycol dibutyl ether, the diethylene glycol dimethyl ethers, dioxane, tetrahydrofuran, the oxiranes, the oxanes, the ethers of higher molecular weight, the crown ethers,
ethyl acetate, ethylene glycol methyl ether acetate, ethylene glycol monoethyl ether acetate, ethylene glycol monobutyl ether acetate, propylene glycol methyl ether acetate, ethylene glycol diacetate, diethylene glycol diacetate, triethylene glycol diacetate, ethylene glycol methyl ether acetate, ethylene glycol ethyl ether acetate, ethylene glycol monobutyl ether acetate, propylene glycol monoethyl ether acetate, ethoxyethyl acetate, diethylene monoethyl ether acetate, dipropylene glycol mono-methyl ether acetate, polyalkylene glycol diesters, e.g., polyethylene glycol diesters, methoxypolyethylene glycol esters,
alkyl carbonates, ethylene carbonate and propylene carbonate,
pyranes and their derivatives,
dichloromethane, trichloromethane, dibromomethane, tribromomethane,
pentane, hexane, cyclohexane, heptane,
paraffinic fractions,
acetonitrile, dimethylformamide, dimethylsulphoxide, hexamethylenephosphoramide, n-methyl-2-pyrrolidinone, nitromethane, pyridine, thiophene.

Particularly advantageously according to the invention, the non-aromatic solvent (II) is present when preparing the compound (I). The solvent used when preparing the compound (I) may be preserved within the thickening agent according to the invention.

Also advantageously, the solvent (II) is partially separated from the thickening agent according to the invention, in particular after preparation of the compound (I) in the solvent (II). Also advantageously, the solvent (II) is completely separated from the thickening agent according to the invention, in particular after preparation of the compound (I) in the solvent (II).

Preferably according to the invention, the reaction between compounds (A2-1) and (A2-2) is conducted in an organic solvent that is non-reactive with the isocyanate group.

Also preferably, the preparation reaction of the monoisocyanate compound (A2) is a catalysed reaction, preferably catalysed with acetic acid, with an amine, preferably 1.8-diazabicyclo[5.4.0]undec-7-ene (DBU), or with at least one derivative of a metal chosen among Al, Bi, Sn, Hg, Pb, Mn, Zn, Zr, Ti, e.g., dibutyl bismuth dilaurate, dibutyl bismuth diacetate, dibutyl bismuth oxide, bismuth carboxylate, dibutyltin dilaurate, dibutyltin diacetate, dibutyltin oxide, a mercury derivative, a lead derivative, zinc salts, manganese salts, a compound comprising chelated zirconium, a compound comprising chelated aluminium. The preferred metal derivative is chosen among a Bi derivative and an Sn derivative.

The thickening agent has particularly advantageous properties that enable its use in many technical fields, particularly in fields implementing fibres.

Advantageously, the thickening agent according to the invention is comprised in a softening composition.

Thus, the invention also provides a softening composition comprising at least one thickening agent according to the invention and at least one softening agent, and optionally water.

The softening composition is usually prepared by mixing the various ingredients, particularly the thickening agent according to the invention and the softening agent, optionally in the presence of water.

According to the invention, the softening agent can be chosen among the softening agents for textile, natural, synthetic or mixed fibres. It can also be chosen among the softening agents for keratin fibre.

Preferably according to the invention, the softening agent is a hydrophobic substance dispersed in an aqueous phase.

Also preferably, the hydrophobic groups of the softening agent comprised in the softening composition according to the invention are hydrocarbon groups, in particular alkyl groups, comprising a number of carbon atoms identical or similar to the number of carbon atoms of the compound (I), particularly the isocyanate compounds (A) and (B). More particularly, the hydrophobic groups of the softening agent comprising a number of carbon atoms identical or similar to the number of carbon atoms of the compound (A2-2).

More preferably according to the invention, the softening agent is chosen among:
- a compound comprising an ester group;
- a compound comprising an amido-amine group;
- a compound comprising an imidazoline group;
- a compound comprising an amine group and at least one hydrocarbon fatty chain, particularly a compound comprising an amine group and at least one hydrocarbon fatty chain as well as at least one ester group;
- a cationic compound comprising a ammonium group and at least one hydrocarbon fatty chain, particularly a cationic compound comprising a ammonium group and at least one hydrocarbon fatty chain as well as at least one ester group.

The salts of chlorine, methoxy sulphonate, ethoxylate or of lactate of these compounds are particularly preferred.

More preferably, the softening composition according to the invention comprises at least one softening agent which is a compound of formula (III):

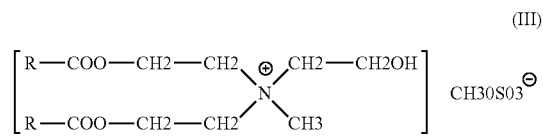

(III)

wherein R represents a straight, branched or cyclic saturated, unsaturated or aromatic hydrocarbon group, preferably a straight, branched or cyclic alkyl group comprising from 8 to 40 carbon atoms or from 8 to 32 carbon atoms, or a straight, branched, or cyclic alkenyl group comprising from 8 to 40 carbon atoms or from 8 to 32 carbon atoms.

The softening agent for the composition according to the invention may be chosen among N,N-dimethyl-9-decenamide, coco pentaethoxy methyl ammonium methosulphate, bis-(acid isopropyl ester) dimethyl ammonium methosulphate, TEA esterquat, or triethanolamine esterquat, imidazoline quat methosulphate of vegetable origin, amidoamine ethoxy quat, amidoamine ethoxylate, amidoamine lactacte, MDIPA-esterquat, or methyldiisopropanolamine dialkyl quat-esterquat, ethoxylated cocoamine quat, mono-oleyl imidazolinium DMS quat, quaternium-72 and propylene glycol, dimethyl sulphate-quaternised tallow diamidoamine, dioleyl amidoamine quat, quaternium-53, di-(oleyl-carboxyethyl)hydroxyethyl methyl ammonium methylsulphate, quaternised tallow diamidoamine, tallow N-diaminoethyl polyethoxy ammonium acetate.

In the softening composition according to the invention, the quantities of thickening agent according to the invention and softening agent may vary, in particular depending on the properties that are sought or the conditions for use of this composition. Preferably, the softening composition according to the invention comprises from 0.001 to 5% by weight of thickening agent according to the invention and from 0.1 to 15% by weight of softening agent.

The thickening agent according to the invention has particularly advantageous properties, in particular when combined with a softening agent.

Thus, the invention provides a method for controlling the viscosity of a softening composition comprising the addition of at least one thickening agent according to the invention.

The thickening agent according to the invention has properties that are also particularly advantageous when it is combined with a lubricating agent, particularly a lubricating agent for textile, natural, synthetic or mixed fibres, or keratin fibres.

Thus, the invention also provides a method for lubricating textile, natural, synthetic or mixed fibres, or keratin fibres comprising the implementation of at least one thickening agent according to the invention.

In addition to a thickening agent comprising a compound (I) and a softening composition and their uses, the invention also relates to certain compounds (I) as such.

Thus, the invention provides a compound (I), prepared in the absence of any diisocyanate compound, by reaction:
(A) of at least one monoisocyanate compound chosen among:
(A1) a compound of formula (II) comprising a single isocyanate group:

R—NCO    (II)

wherein R represents a group chosen among:
a straight, branched or cyclic, saturated, unsaturated, or aromatic hydrocarbon group comprising from 8 to 40 carbon atoms or from 8 to 32 carbon atoms, except for a straight, branched or cyclic saturated, unsaturated, or aromatic hydrocarbon group comprising 20 carbon atoms; and
(A2) at least one monoisocyanate compound from the separate reaction
(A2-1) of at least one compound comprising at least one labile hydrogen atom chosen among a straight, branched, or cyclic $C_{10}$-$C_{40}$ or $C_{10}$-$C_{32}$ monohydric alcohol, preferably $C_{10}$-$C_{30}$, more preferentially $C_{10}$-$C_{24}$, even more preferentially $C_{14}$-$C_{22}$, except for a straight, branched or cyclic $C_{12}$ monohydric alcohol and a straight, branched, or cyclic $C_{14}$ monohydric alcohol; and
(A2-2) of at least one asymmetric diisocyanate compound;
(B) of at least one isocyanate compound comprising more than 2 isocyanate groups; and
(C) of at least one compound of formula (I):

(HO)-$L_n$-(OH)    (I)

wherein L independently represents a polyalkylene glycol residue and n represents a number ranging from 40 to 400.

Advantageously, the compound (I) according to the invention is a compound with a hydrophilic character. It can be formulated in an aqueous medium.

Preferably, the compound (I) according to the invention is prepared from a compound (A1) of formula (II) comprising a single isocyanate group, wherein R represents a group chosen among a straight, branched, or cyclic saturated, unsaturated or aromatic hydrocarbon group comprising from 8 to 19 carbon atoms or from 8 to 18 carbon atoms.

Also preferably, the compound (I) according to the invention is prepared from a compound (A1) of formula (II) comprising a single isocyanate group, and wherein R represents a straight, branched or cyclic, saturated, unsaturated, or aromatic hydrocarbon group comprising from 21 to 40 carbon atoms or from 21 to 32 carbon atoms or from 22 to 40 carbon atoms or from 22 to 32 carbon atoms.

More preferably, the compound (I) according to the invention is prepared from a compound (A1) of formula (II) comprising a single isocyanate group, and wherein R represents:
a straight, branched, or cyclic alkyl group comprising from 8 to 19 carbon atoms or from 8 to 18 carbon atoms; or
a straight, branched, or cyclic or aromatic alkenyl group comprising from 8 to 19 carbon atoms or from 8 to 18 carbon atoms.

More preferably, the compound (I) according to the invention is prepared from a compound (A1) of formula (II) comprising a single isocyanate group, and wherein R represents:
a straight, branched, or cyclic alkyl group comprising from 8 to 11 carbon atoms or 13 carbon atoms or from 15 to 18 carbon atoms or from 15 to 19 carbon atoms; or
a straight, branched, or cyclic or aromatic alkenyl group comprising from 8 to 11 carbon atoms or from 8 to 11 carbon atoms or 13 carbon atoms or from 15 to 18 carbon atoms or from 15 to 19 carbon atoms.

Also more preferably, the compound (I) according to the invention is prepared from a compound (A1) of formula (II) comprising a single isocyanate group, and wherein R represents:
a straight, branched, or cyclic alkyl group comprising from 21 to 40 carbon atoms or from 21 to 32 carbon atoms or from 22 to 40 carbon atoms or from 22 to 32 carbon atoms; or
a straight, branched, or cyclic or aromatic alkenyl group comprising from 21 to 40 carbon atoms or from 21 to 32 carbon atoms or from 22 to 40 carbon atoms or from 22 to 32 carbon atoms.

Essentially, the compound (I) according to the invention is prepared in the absence of any diisocyanate compound. In fact, the monoisocyanate compound (A) is either a monoisocyanate compound (A1) or a monoisocyanate compound (A2) derived from the condensation of compounds (A2-1) and (A2-2), whereas the isocyanate compound (B) comprises more than 2 isocyanate groups.

Thus, when preparing the compound (I) according to the invention, the compound (C) implemented reacts with the monoisocyanate compound (A) and with the isocyanate compound (B) comprising more than 2 isocyanate groups.

The invention therefore provides a method of preparing a compound (I) according to the invention, by reaction, in the absence of any diisocyanate compound:
(A) of at least one compound chosen among:
(A1) a compound comprising a single isocyanate group and
(A2) at least one monoisocyanate compound from the separate reaction
(A2-1) of at least one compound comprising at least one labile hydrogen atom and
(A2-2) of at least one asymmetric diisocyanate compound,
(B) of at least one isocyanate compound comprising more than 2 isocyanate groups, and
(C) of at least one compound of formula (I):

(HO)-$L_n$-(OH)    (I)

wherein L independently represents a polyalkylene glycol residue and n represents a number ranging from 40 to 400.

Advantageously, the method of preparation according to the invention can be performed in the presence of at least one solvent that is non-reactive with the isocyanate group. Preferably, it is a non-aromatic solvent (II) according to the invention, more preferentially an aprotic solvent that is non-reactive with the isocyanate group. Preparation can be performed at solvent reflux temperature.

The compound (I) according to the invention has particularly advantageous properties, in particular when it is combined with a softening agent or when it is present in a softening composition.

Thus, the invention provides a method for controlling the viscosity of a softening composition comprising the addition of at least one compound (I) according to the invention or a compound (I) prepared according to the method of preparation according to the invention.

The compound (I) according to the invention has properties that are particularly advantageous, in particular when it is combined with a lubricating agent for textile, natural, synthetic or mixed fibres, or keratin fibres.

Thus, the invention also provides a method for lubricating textile, natural, synthetic or mixed fibres, or keratin fibres, comprising the implementation of at least one compound (I) according to the invention or a compound (I) prepared according to the method of preparation according to the invention.

The following examples illustrate the various aspects of the invention.

EXAMPLE 1

Preparation of Urethane Compounds (I) According to the Invention

In a 3 L glass reactor (container 1) equipped with a mechanical stirring rod, vacuum pump, and nitrogen inlet, and heated by means of a jacket in which oil circulates, 514.8 g of polyethylene glycol with a molecular mass ($M_w$) of 10,000 g/mol (PEG 10,000) is placed as compound (C1) along with 514.8 g of ethylene diglycol monoethyl ether acetate (EDGA—CAS number 112-15-2) as compound (II). The stirred medium is heated to 100° C. and placed in an inert atmosphere.

Additionally, in a 250 mL three-necked glass flask (container 2), 34.29 g of isophorone diisocyanate (IPDI) is placed as compound (A2-2), to which is added 1 g of a bismuth catalyst (bismuth carboxylate). The medium is purged with nitrogen and then heated to 50° C. When this temperature is reached, 37.38 g of hexadecan-1-ol is injected with a syringe into container 2, as compound (A2-1). When the injection is completed, the reaction mixture of container 2 is left to stir for 15 minutes. A urethane compound (A) is obtained according to the invention.

Next, 13.14 g of HDI isocyanurate is added to container 2, as compound (B) and left to stir for 5 minutes.

Then, the contents of container 2, comprising the admixture of monoisocyanate compound (A) and triisocyanate compound (B), are poured into container 1. Stirring is continued for 60 minutes at 100±2° C. Then the NCO group level is checked to ensure it is null, indicating the end of the reaction.

A thickening agent (AE1) according to the invention is obtained comprising the urethane compound (I-1) and EDGA as a non-reactive solvent (II) according to the invention.

The mixture of compounds (I-1) and (II) is formulated by adding, in succession, 150 g of alkyl-ethoxylated surfactant (Disponil D8 from BASF) (TA), 1,722 g of water and 3 g of biocide (Biopol SMV from Chemipol).

A thickening formulation (FE1) comprising the thickening agent (AE1) is obtained according to the invention.

Similarly, other urethane compounds (I) are prepared (compounds (I-2) to (I-6)), then thickening agents (AE2) to (AE6) are prepared, and lastly thickening formulations (FE2) to (FE6) according to the invention comprising thickening agents (AE2) to (AE6), respectively. The respective reagents and proportions (% by mass) are shown in Table 1, in particular tetraethylene glycol dimethyl ether or TEGDE (CAS number 112-49-2) as another solvent (II) according to the invention.

The thickening formulations (FE1) to (FE6) according to the invention are liquid at room temperature; their Brookfield viscosity was measured at 100 rpm and at 25° C.

TABLE 1

| | Thickening formulation | | | | | |
|---|---|---|---|---|---|---|
| | (FE1) | (FE2) | (FE3) | (FE4) | (FE5) | (FE6) |
| Compound (I) | (I-1) | (I-2) | (I-3) | (I-4) | (I-5) | (I-6) |
| (A2-1) hexadecan-1-ol | 1.3 | 1.3 | 1.3 | 1.5 | 1.2 | 1.2 |
| (A2-2) IPDI | 1.1 | 1.1 | 1.2 | 1.4 | 1.1 | 1.1 |
| (B) HDI isocyanurate | 0.4 | 0.4 | | 0.2 | 0.4 | 0.4 |
| (B) HDI biuret | / | / | 0.2 | / | / | / |
| (C) PEG8000 | / | / | | 16.8 | / | / |
| (C) PEG10000 | 17.2 | 17.3 | 17.4 | | 17.2 | 17.2 |
| Bi catalyst | 0.01 | 0.01 | 0.01 | 0.01 | 0.01 | 0.01 |
| EDGA solvent (II) | 17.2 | 17.3 | 17.4 | 16.8 | 17.2 | / |
| TEGDE solvent (II) | / | / | / | / | / | 17.3 |
| Biocide | 0.1 | 0.1 | 0.1 | 0.1 | 0.1 | 0.1 |
| TA | 5.0 | 5.0 | 5.0 | 5.0 | 5.0 | 5.0 |
| Water | 57.6 | 57.6 | 57.5 | 58.1 | 57.7 | 57.6 |
| Viscosity (mPa · s) | 7,000 | 7,100 | 2,900 | 3,950 | 7,600 | 9,800 |

EXAMPLE 2

Preparation and Assessment of Thickening Compositions According to the Invention and Comparative Thickening Compositions A softening composition (CA1) is prepared according to the invention by preparing 50 g of methyl bis[ethyl (tallow)]-2-hydroxyethyl ammonium methyl sulphate (Stepantex VT 90 by Stepan) melted at a temperature of 50° C. and then pouring the melted product into 950 g of stirred deionised water and bringing it to a temperature of 50° C.

After the softening agent has been fully added, stirring is continued for 30 minutes at a temperature of 50° C. Heating is stopped and the mixture is left to stir until it has cooled to room temperature.

To 100 g of this mixture, 0.29 g of thickening formulation (FE1) according to the invention is added while stirring; it is left to stir for 30 minutes.

Next, the effectiveness of the thickening agent according to the invention is assessed using a Haake Mars III viscosity meter with a planar cone measurement system. Viscosity measurement (mPa·s) is performed at 18.17 s$^{-1}$ after 1 day and after 5 days.

Similarly, other softening compositions (CA2), (CA3), (CA4), and (CA5) according to the invention are prepared comprising the thickening formulations (FE2), (FE3), (FE5) and (FE6), respectively, as well as a comparative softening composition (CC1) comprising a known polyurethane thickening agent (0.29 g of Dow Acusol 882 at a concentration of 17.5% by weight in solvent) rather than a thickening agent according to the invention. The results obtained are shown in Table 2.

TABLE 2

| Softening composition | Viscosity at 1 day | Viscosity at 5 days |
|---|---|---|
| (CA1) | 362 | 416 |
| (CA2) | 398 | 426 |
| (CA3) | 285 | 267 |
| (CA4) | 330 | 361 |
| (CA5) - 0.28 g (FE6) | 317 | 342 |
| (CC1) | 180 | 258 |

For comparable amounts of thickening formulation with regard to the comparative softening composition comprising a known polyurethane thickening agent, the softening compositions according to the invention have much higher viscosities. The thickening agents according to the invention that were implemented are more effective than the known polyurethane thickening agent.

EXAMPLE 3

Preparation and Assessment of a Thickening Composition According to the Invention and a Comparative Thickening Composition A softening composition (CA6) according to the invention is prepared comprising the thickening formulation (FE5) according to the invention and a comparative softening composition (CC2) comprising a known polyurethane thickening agent (Dow Acusol 882 at a concentration of 17.5% by weight in a solvent) rather than a thickening agent according to the invention.

A comparison is then made of the amounts of thickening formulation required to obtain an identical or comparable viscosity for the two softening compositions. 200 g of a known softening composition comprising no thickening agent (ADCO Velveta) is placed under stirring and an amount of thickening formulation is added and then it is left to stir for 30 minutes.

Viscosity (in mPa·s) is measured at room temperature using a Brookfield viscosity meter at 20 rpm. This measurement is performed immediately after stirring at the time of preparation and after 21 and 28 days of storage at room temperature. The results obtained are shown in Table 3.

TABLE 3

| Velveta Softening Composition | 200 g | 200 g |
|---|---|---|
| (CA6) | 0.16 g | / |
| (CC2) | / | 0.59 g |
| Storage time (days) | Viscosity | |
| 0 | 2,949 | 2,689 |
| 21 | 2,689 | 2,689 |
| 28 | 2,699 | 1,970 |

The initial viscosity of the softening composition according to the invention and its viscosity at 21 days and 28 days are equal to or well above the viscosities of the softening composition prepared from a known polyurethane thickening agent. Moreover, the softening composition according to the invention comprises a very low amount of thickening agent.

EXAMPLE 4

Preparation and Assessment of a Thickening Composition According to the Invention and Comparative Thickening Compositions Similar to Example 3, a softening composition (CA7) according to the invention is prepared comprising the thickening formulation (FE5) and 3 comparative softening compositions (CC3), (CC4) and (CC5) are prepared comprising various known thickening agents rather than a thickening agent according to the invention.

The comparative softening composition (CC3) comprises a known polyurethane thickening agent (Dow Acusol 882 at a concentration of 17.5% by weight in solvent). The comparative softening composition (CC4) comprises a known thickening agent (Rheovis CDE by BASF, at a concentration of at least 50% by weight in a solvent blend).

The comparative softening composition (CC5) comprises a known thickening agent (Flosoft 222 by Snf at a concentration of 56% by weight in solvent).

200 g of a known softening composition comprising no thickening agent (ADCO Velveta) is placed under stirring and an amount of thickening formulation is added and then it is left to stir for 30 minutes.

Next, the effectiveness of the thickening agent according to the invention is assessed using a Haake Mars III viscosity meter with a planar cone measurement system. Viscosity measurement (mPa·s) is performed at 18.17 s$^{-1}$ after 1 day. The results obtained are shown in Table 4.

TABLE 4

| Velveta Softening Composition | 100 g | 100 g | 100 g | 100 g |
|---|---|---|---|---|
| (CA7) | 0.079 g | | | |
| (CC3) | | 0.0825 g | | |
| (CC4) | | | 0.0815 g | |
| (CC5) | | | | 0.0807 g |
| Storage time (days) | Viscosity measured at 18.17 s$^{-1}$ | | | |
| 1 | 252 | 91 | 74 | 61 |

The viscosity of the softening composition according to the invention is much higher than the viscosity of the various softening compositions prepared from the known thickening agents.

The invention claimed is:

1. A thickening agent, comprising:
   I. a compound prepared by reaction of compounds (A), (B), and (C), wherein said compounds (A), (B), and (C) are free of any diisocyanate compound, and wherein:
   (A) is at least one monoisocyanate compound chosen from:
      (A1) a compound comprising a single isocyanate group and
      (A2) at least one monoisocyanate compound from a separate reaction of (A2-1) at least one compound comprising a labile hydrogen atom and (A2-2) at least one asymmetric diisocyanate compound, (B) is at least one isocyanate compound comprising more than 2 isocyanate groups, and (C) is at least one compound of formula (I):

(HO)-L$_n$-(OH)  (I)

wherein L independently represents a polyalkylene glycol residue and n represents a number ranging from 40 to 400; and II. a solvent which is non-aromatic, non-reactive with the isocyanate group and at least one selected from the group consisting of a ketone, an ether, an aprotic ethyl derivative, a diether, a crown ether, an ester, a diester, a carbonate, a furan, a halogenated solvent, an alkane, an alkene, an alkyne, a nitrogenous or sulphurous solvent, a mineral oil and a silicone oil.

2. The thickening agent according to claim 1, in which the compound (A1) is:
a compound of formula (II):

R—NCO  (II)

wherein R represents a straight, branched or cyclic saturated, unsaturated or aromatic hydrocarbon group; or
a compound selected from the group consisting of:
an aromatic monoisocyanate compound;
a polyfunctional aromatic monoisocyanate compound;
an alkyl monoisocyanate compound; and
a cycloalkyl monoisocyanate compound.

3. The thickening agent according to claim 2, in which the compound (A1) is a compound of formula (II) wherein R represents:
a straight, branched, or cyclic saturated, unsaturated or aromatic hydrocarbon group comprising from 10 to 32 carbon atoms.

4. The thickening agent according to claim 1, in which the at least one compound (A2-1) is selected from the group consisting of a compound comprising a labile hydrogen atom that is reactive with the asymmetric diisocyanate compound; a compound comprising at least one hydroxyl group; a compound comprising a primary amine group or a secondary amine group; a carboxylic acid; and a mercaptan compound.

5. The thickening agent according to claim 1, in which the at least one asymmetric compound (A2-2) is selected from the group consisting of:
an asymmetric aromatic diisocyanate compound; and
an asymmetric alicyclic diisocyanate compound.

6. The thickening agent according to claim 1, in which:
the at least one isocyanate compound (B) is an isocyanate compound comprising more than 2.2 isocyanate groups, the at least one isocyanate compound (B) is triphenylmethane-4,4',4"-triisocyanate or 1,1',1"-methylidynetris (4-isocyanatobenzene), the at least one isocyanate compound (B) is an isocyanurate compound, or the at least one isocyanate compound (B) is a biuret trimer compound.

7. The thickening agent according to claim 1, in which the at least one compound (C) is a compound of formula (I) wherein:
L independently represents a polyethylene glycol residue; and/or
n represents a number ranging from 50 to 400.

8. The thickening agent according to claim 1, in which the at least one compound (C) of formula (I) has a molecular mass ($M_w$) ranging from 1,500 to 20,000 g/mol.

9. The thickening agent according to claim 1, in which a molar amount of the at least one monoisocyanate compound (A) is approximately twice as high as a molar amount of the at least one compound (C).

10. The thickening agent according to claim 1, in which the solvent (II) is present when preparing the compound (I).

11. The thickening agent according to claim 1, in which the solvent (II) is partially separated.

12. The thickening agent according to claim 1, in which the solvent (II) is completely separated.

13. A softening composition, comprising:
the thickening agent according to claim 1,
a softening agent, and
optionally water.

14. The softening composition according to claim 13, in which:
the softening agent is selected from the group consisting of a softening agent for textile, natural, synthetic or mixed fibres, and a softening agent for keratin fibre; or
the softening agent is a hydrophobic substance dispersed in an aqueous phase.

15. The softening composition according to claim 13, in which the softening agent is
a compound comprising an ester group,
a compound comprising an amido-amine group,
a compound comprising an imidazoline group,
a compound comprising an amine group and at least one hydrocarbon fatty chain or
a cationic compound comprising an ammonium group and at least one hydrocarbon fatty chain.

16. A method for controlling the viscosity of a softening composition of claim 13, the method comprising adjusting the quantity of said thickening agent.

17. A method for lubricating textile, natural, synthetic or mixed fibres, or keratin fibres comprising implementing at least one thickening agent according to claim 1.

* * * * *